(12) United States Patent
Wood et al.

(10) Patent No.: US 8,608,811 B2
(45) Date of Patent: Dec. 17, 2013

(54) COMPOSITION AND PROCESS FOR OXIDATIVE COLOURING KERATIN FIBERS

(75) Inventors: Jonathan Wood, Weinheim (DE); Sabine Schäfer, Rüsselsheim (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/993,459

(22) PCT Filed: Dec. 23, 2011

(86) PCT No.: PCT/EP2011/074012
§ 371 (c)(1),
(2), (4) Date: Jun. 12, 2013

(87) PCT Pub. No.: WO2012/089688
PCT Pub. Date: Jul. 5, 2012

(65) Prior Publication Data
US 2013/0263877 A1    Oct. 10, 2013

(30) Foreign Application Priority Data
Dec. 27, 2010  (EP) ..................................... 10016087

(51) Int. Cl.
*A61Q 5/10*  (2006.01)
(52) U.S. Cl.
USPC ................ 8/405; 8/406; 8/435; 8/552; 8/553; 8/554; 8/581; 8/607
(58) Field of Classification Search
USPC ............. 8/405, 406, 435, 552, 553, 554, 581, 8/607
See application file for complete search history.

(56) References Cited

U.S. PATENT DOCUMENTS 4,808,190 A    2/1989  Grollier et al.

FOREIGN PATENT DOCUMENTS

| EP | 2 177 203 A1 | 4/2010 | |
| EP | 2177203 A1 * | 4/2010 | ............... A61Q 5/10 |
| EP | 2 246 097 A1 | 11/2010 | |

OTHER PUBLICATIONS

STIC Search Report dated Jul. 24, 2013.*
International Search Report mailed Jun. 8, 2012.

* cited by examiner

*Primary Examiner* — Eisa Elhilo
(74) *Attorney, Agent, or Firm* — Norris McLaughlin & Marcus, P.A.

(57) ABSTRACT

The present invention relates to a process for oxidative coloring keratin fibers especially human hair wherein dyeing composition comprises a cross linked copolymer. The objective of the present invention is a process for oxidative coloring hair wherein compositions A and B are mixed, composition A comprises at least one oxidative dye precursor and optionally at least one coupling agent and optionally at least one direct dye in a cosmetically acceptable medium and composition B comprises at least one oxidizing agent in a cosmetically acceptable medium, and applied onto hair and processed for 1 to 45 min at a temperature range of 20 to 45° C. and rinsed off from hair, wherein at least one of the two compositions A and B comprises a cross linked copolymer of vinylpyrrolidone, vinylimidazol, 3-methyl-1-vinylimidazolium and methacrylic acid.

15 Claims, No Drawings

COMPOSITION AND PROCESS FOR OXIDATIVE COLOURING KERATIN FIBERS

This application is a 371 application of PCT/EP2011/074012 filed Dec. 23, 2011, which claims foreign priority benefit under 35 U.S.C. §119 of European Application No. 10016087.8 filed Dec. 27, 2010.

The present invention relates to a composition and a process for oxidative coloring keratin fibers especially human hair wherein dyeing composition comprises a cross linked copolymer.

Oxidative coloring is carried out by applying onto hair a mixture of two compositions which are kept separate till short before application and after certain processing time the hair is rinsed off. For a successful color result, it is very important that the applied dyeing agent stays at the site of application during the entire period of processing. Currently, emulsions with certain consistency and also thickened compositions are used in practice. The drawbacks are practicing with highly sensible compositions such as instability of emulsions in the presence of high salt concentrations on one hand, and on the other hand, inacceptable hair properties in terms of combability, flyaways, elasticity when conventional thickeners are used. Due to inacceptable hair conditioning and feel, consumers often have to use additional products in order to restore and/or bring hair feel to a acceptable level. This is on one hand time consuming and on the other hand brings unnecessary additional costs.

The aim of the present invention is to provide a hair dyeing process with compositions having appropriate consistency after mixing and also leave hair in a cosmetically acceptable form so that use of additional hair cosmetic compositions is largely avoided.

The objective of the present invention is a process for oxidative coloring hair wherein compositions A and B are mixed, composition A comprises at least one oxidative dye precursor and optionally at least one coupling agent and optionally at least one direct dye in a cosmetically acceptable medium and composition B comprises at least one oxidizing agent in a cosmetically acceptable medium, and applied onto hair and processed for 1 to 45 min at a temperature range of 20 to 45° C. and rinsed off from hair, wherein at least one of the two compositions A and B comprises a cross linked copolymer of vinylpyrrolidone, vinylimidazol, 3-methyl-1-vinylimidazolium and methacrylic acid.

Further objective of the present invention is the use of the inventive process for homogeneous colouring and conditioning of keratin fibers, especially human hair.

In a preferred embodiment of the present invention, both compositions A and B comprise a cross linked copolymer of vinylpyrrolidone, vinylimidazol, 3-methyl-1-vinylimidazolium and methacrylic acid.

Suitable and the most preferred polymer is Polyquaternium-86 which is commercially available under the trade name Luvigel Advanced from BASF.

Still further object of the present invention is a composition comprising at least one hair dye and a cross linked copolymer of vinylpyrrolidone, vinylimidazol, 3-methyl-1-vinylimidazolium and methacrylic acid, wherein at least one hair dye is preferably selected from oxidative hair dye precursors and direct dyes which may be anionic, cationic and neutral dye. Further preferred embodiment of the present invention is that the composition comprises at least one oxidizing agent, preferably hydrogen peroxide.

Concentration of the polymer is in the range of 0.01 to 10%, preferably 0.05 to 7.5, more preferably 0.1 to 5% and most preferably 0.2 to 5% by weight calculated to total of each composition.

Composition A, or a composition for dyeing as described above, comprises at least one oxidative dye precursor. Non-limiting examples to developers are p-phenylenediamines and substituted p-phenylenediamines such as 2,5-diaminotoluene, 2-n-propyl or 2-ethyl-p-phenylenediamine, 2,6-dimethyl-p-phenylenediamine, 2-(2,5-diaminophenyl)ethanol, 1-amino-4-bis-(2'-hydroxyethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 2-aminophenol, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, 5-amino salicylic acid and/or 1,2,4-triamino benzene or the water-soluble salts thereof.

Suitable tetraminopyrimidines are in particular 2,4,5,6-tetraminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof; a preferred amino-substituted triazine is 2,4-diamino-1,3,5-triazine.

Composition A or a composition for dyeing as described above, furthermore optionally comprises at least one coupling agent. Suitable non-limiting examples are resorcinol, 2-methyl resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxy-ethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

However, this shall not exclude the addition of further developing and coupling substances.

The total concentration of the developing substances customarily ranges between about 0.05% and 5%, preferably 0.1% and 4%, in particular 0.25% to 3% by weight, calculated to the total hair dyeing composition excluding the oxidation agent.

In the hair dyeing compositions, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition excluding the oxidizing agent.

The preferred weight proportion of the named developing substances to the coupling substances ranges between about 1:8 to 8:1, preferably about 1:5 to 5:1, in particular 1:2 to 2:1.

Oxidative colouring compositions, Composition A, a composition for dyeing as described above, comprises direct dyes of neutral, cationic and anionic ones.

Non-limiting examples to neutral HC dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic Acid, 1,2-Diamino-4-nitrobenzol, 1,4-Diamino-2-nitrobenzol, 3-Nitro-4-aminophenol, 1-Hydroxy-2-amino-3-nitrobenzol, 2-Hydroxyethylpicramic acid, 2-amino-4.6-dinitrophenol, 2-amino-4-nitrophenol, and 2-amino-6-chloro-4-nitrophenol.

Cationic direct dyes as disclosed in the patent applications EP 1166752, EP 1172082 and EP 970684 and as well WO 95/01772 are suitable for the composition A of the present invention. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 87, Basic Yellow 57, and Basic Orange 31. Preferred cationic dyes are especially Basic Yellow 87, Basic Orange 31 and Basic Red 51.

Suitable non-limiting examples to anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Concentration of one or more direct dyes in total is in the range of 0.001 to 5% by weight, preferably 0.01 to 4% more preferably 0.05 to 3% and most preferably 0.1 to 2.5% by weight calculated to total composition.

Composition A, a composition for dyeing as described above, comprises additionally at least one alkalizing agents. Suitable ones are ammonia and alkyl or alkanol amines such as monoethanol amine, triethanol amine etc. Concentration of alkalizing agent is dependent on the alkalinity value aimed is in the range of 0.1 to 20%, preferably 0.2 to 15% and more preferably 0.5 to 10% by weight calculated to total composition excluding oxidizing agent.

Composition B, a composition for dyeing as described above, comprises at least one oxidizing agent. The preferred oxidizing agent is hydrogen peroxide, for example in a concentration of 2 to 12% by weight. However, the use of other peroxides such as urea peroxide and melamine peroxide is also possible.

The pH-value of the ready-to-use hair dyeing composition, i.e. after mixing with peroxide, is in the range of 2 to 11, preferably 5 to 10.5, more preferably 6 to 10 and most preferably 6.5 to 9.5.

Ready to use composition of the present invention has a viscosity in the range of 1000 to 25000 mPa·s measured at 20° C. with Brookfield viscometer using an appropriate spindle. Preferably the viscosity of the ready to use composition is in the range of 2500 to 20000 mPa·s and more preferably 5000 to 20000 mPa·s. and most preferably 7500 to 15000 mPa·s. measured at 20° C.

In a further preferred embodiment of the present invention, a pretreatment composition is applied onto hair prior to application of oxidative dyeing composition. Pretreatment composition comprises at least one compound such as inorganic salt and/or dihydroxyacetone which catalyzes and/or affects the oxidative colour development reaction from oxidative dyes precursors, and optionally rinsed off from hair. Suitable non-limiting inorganic salts are salts of iodide ions especially potassium and sodium salts, copper chloride, copper sulphate, cobalt chloride, cerium sulphate, cerium chloride, vanadium sulphate, lithium chloride, potassium dichromate, magnesium acetate, calcium chloride, calcium nitrate, barium nitrate, magnesium oxide, ammonium nitrate and ammonium chloride. Preferred are salts of iodide ions especially potassium and sodium salts, copper chloride, copper sulphate, cobalt chloride, cerium sulphate, cerium chloride, vanadium sulphate, lithium chloride, potassium dichromate, magnesium acetate, calcium chloride, calcium nitrate, barium nitrate and magnesium oxide. Most preferred are the salts of iodide ions and especially sodium and potassium salts and in particular potassium iodide. It is furthermore appropriate to use suitably any combination of inorganic salts, two or more salts, catalyzing and/or effecting the oxidative colour development reaction from oxidative dyes precursors.

Concentration of at least one inorganic salt and/or dihydroxyacetone in the aqueous composition is typically from 0.01 to 20%, preferably 0.05 to 15% and most preferably 0.1 to 10% and in particular 0.2 to 7.5% by weight calculated to the total composition. The concentration ranges disclosed herein are the total concentration of the inorganic salts in case more then one is used in mixture.

In a preferred embodiment, aqueous composition comprising at least one inorganic salt is processed up to 20 min, preferably up to 15 min and more preferably up to 10 min with or without using heat, preferably at a temperature range between 20 and 45° C., on hair prior to application of oxidative dyeing composition.

In a preferred embodiment of the present invention, pretreatment composition comprises as well a cross linked copolymer of vinylpyrrolidone, vinylimidazol, 3-methyl-1-vinylimidazolium and methacrylic acid, preferably Polyquaternium-86 at the above mentioned concentration ranges.

Viscosity of the pretreatment composition is also in the range of 1000 to 25000 mPa·s measured at 20° C. with Brookfield viscosmeter using an appropriate spindle. Preferably the viscosity of the pretreatment composition is in the range of 2500 to 20000 mPa·s and more preferably 5000 to 20000 mPa·s. and most preferably 7500 to 15000 mPa·s. measured at 20° C.

pH of the pretreatment composition is preferably in the range of 5 to 10.

Any of the aqueous compositions used in the inventive process of the present invention as disclosed above can comprise one or more of the following ingredients.

One or more of aqueous compositions may comprise additional thickening polymer of any kind, namely, anionic, cationic, nonionic and/or amphoteric polymers. Natural polymers such as chitosan and its derivatives, cellulose and its derivatives and hydroxyethylcellulose and guar gum and their derivatives may be comprised in any of the aqueous compositions used in the novel process of the present invention. It should be noted that the concentration of the additional thickening polymer should be lower than the concentration of the cross linked copolymer of vinylpyrrolidone, vinylimidazol, 3-methyl-1-vinylimidazolium and methacrylic acid, preferably Polyquaternium-86.

One or more of aqueous compositions may comprise cationic polymers as conditioning agents which enhances first of all combability and therefore makes applications onto hair easier which may also additionally have thickening effect. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore. chitosan and chitin can also be included in the compositions as cationic natural polymers.

Furthermore, those cationic polymers known with their CTFA category name Polyquaternium may as well be added into pre-treatment compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 87, Polyquaternium 67.

The cationic polymers also include the quaternized products of graft polymers from organopolysiloxanes and polyethyl oxazolines described in EP-A 524 612 and EP-A 640 643.

Concentration of the polymers of anionic, cationic, nonionic and/or amphoteric or zwitterionic character mentioned above is in the range of 0.05-10%, preferably 0.1-7.5%, preferably 0.2-7.5% and most preferably 0.2-5% by weight, calculated to the total composition.

One or more of aqueous compositions of inorganic salt may comprise one or more surfactants selected from nonionic, anionic, cationic and amphoteric ones. The surfactants suitable for the compositions are nonionic surfactants. Preferred nonionic surfactants are ethoxylated fatty alcohols according to the following formula:

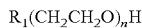

where $R_1$ is a saturated or unsaturated, linear or branched alkyl chain with 12 to 22 C atoms and n is a number between 2 and 50 preferably 2 to 40, more preferably 2 to 30. In one of the preferred embodiments of the invention, the hair treatment compositions comprise a mixture of two nonionic fatty alcohol ethoxylates, one has between 2 to 10 ethoxylate units and the other is more than 10. Those surfactants are known by the generic terms for example "Laureth", "Myristeth", "Oleth", "Ceteth", "Deceth", "Steareth" and "Ceteareth" according to the CTFA nomenclature, including addition of the number of ethylene oxide molecules. e.g. Ceteareth-20, Steareth-2.

Further nonionic surfactants suitable are those polyethylene glycol ethers of monoglycerides according to the general formula

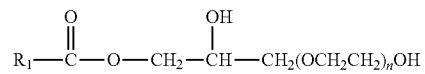

$R_1$ and n are same as above. Examples to those types of nonionic surfactants are PEG-7-glyceryl cocoate known with the trade name Cetiol HE from Cognis, PEG-8-glyceryl laurate know with the trade name Glycerox L8 from Croda Chemicals, PEG-10 glyceryl oleate, PEG-15 glycerryl isostearate, PEG-5 glycerryl stearate, PEG-15 glyceryl ricinoleate, etc.

Further nonionic surfactants suitable are alkyl polyglucosides of the general formula

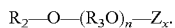

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Additionally useful nonionic surfactants are the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Still further suitable nonionic surfactants are amineoxides. Such amineoxides are known especially because of their use in cleansing compositions, for example $C_{12}$-$C_{18}$-alkyl dimethyl aminoxides such as lauryl dimethyl aminooxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain, Those are on the market, for example, under the trade names "Ammonyx®", "Aromox®" or "Genaminox®".

Anionic surfactants of the sulfate, sulfonate, carboxylate types are as well suitable in compositions of the present invention. Those are the ones very commonly used in cosmetic cleansing preparations, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_6-(C_2H_4O)_n-O-CH_2COOX.$$

wherein $R_6$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula $$R_6-\underset{\underset{O}{\|}}{C}-\underset{\underset{H}{|}}{N}-CH_2-CH_2-(C_2H_4O)_n-CH_2COOX$$

wherein $R_6$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in mixture with other anionic surfactants, as well as sulfofatty acids and the esters thereof.

It is also possible to use mixtures of several anionic surfactants in mixture within the scope of the invention.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

As further surfactant component, one or more of aqueous compositions may comprise amphoteric or zwitterionic surfactants.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Cationic surfactants may also be comprise in one or more aqueous compositions and particularly as conditioning agent and according to the general formula $$R_8-\underset{\underset{R_{11}}{|}}{\overset{\overset{R_9}{|}}{N^+}}-R_{10}\ X^-$$

where $R_8$ is a saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has typical value of 0-4 or $$R_{13}COO(CH_2)_n$$

where $R_{13}$ is saturated or unsaturated, branched or non-branched alkyl chain with 7-21 C atoms and n has typical value of 0-4. and $R_9$ is a lower alkyl chain with 1 to 4 carbon atoms, saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has typical value of 0-4 or $$R_{13}COO(CH_2)_n$$

where $R_{13}$ is saturated or unsaturated, branched or non-branched alkyl chain with 7-21 C atoms and n has typical value of 0-4. and $R_{10}$ and $R_{11}$ are independent from each other lower alkyl chain with 1 to 4 carbon atoms, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, especially preferred as hair conditioning agents are those compounds known per se and are on the market, for example, under the trade names "Schercoquat®", "Dehyquart® F30" and "Tetranyl®".

Again from the above quaternary ammonium compounds disclosed with the general formula, especially preferred as conditioning ingredient are these compounds are known per se and on the market, for example, under the trade name "INCROQUAT® HO" or "OCS". Those compounds are known with a general ingredient category under "amidoquat" in the cosmetic industry.

According to present invention total concentration of surfactants of anionic, cationic, non-ionic and/or amphoteric or zwitterionic character is in the range of 0.05-10%, preferably 0.05-7.5% and most preferably 0.05-5% by weight, calculated to the total composition of each composition.

One or more of aqueous composition can also comprise conditioning agents selected from oily substances and non-ionic substances. Oily substances are selected from such as silicone oils volatile or non-volatile, natural and synthetic oils. Among silicone oils those can be added include dimethicone, dimethiconol, polydimethylsiloxane, DC fluid ranges from Dow Corning, arylated silicones, aminated silicones, natural oils such as olive oil, almond oil, avocado oil, wheatgerm oil, ricinus oil and the synthetic oils, such as mineral oil.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters.

Conditioners mentioned above can be contained at a concentration of below 1%, preferably below 0.75% by weight, calculated to total composition.

One or more of the aqueous compositions can comprise one or more organic solvent. Examples are such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of one or more organic solvents is in the range of 1 to 25%, preferably 1 to 20%, more preferably 1 to 15% and most preferably 1 to 10% by weight, calculated to the total composition.

One or more of the compositions may comprise at least one ubiquinone of the formula

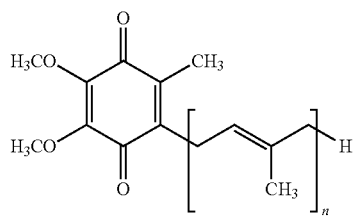

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total of each composition.

The compositions comprise ubiquinone which is preferably selected from the ones where n is a number between 6 and 10 and more preferably it is ubichinone 50 where n is 10, also known as Coenzyme Q10.

One or more of the aqueous composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

One or more of the aqueous composition can comprise further ceramide type of compound with the general formula

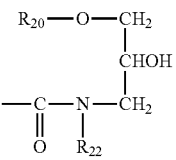

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Optionally fatty acids of $C_{10}$ to $C_{22}$ may be incorporated into the compositions of the present invention at a concentration of preferably 0.01 to 2.5% by weight calculated to total of each composition.

In a further preferred embodiment of the present invention, One or more of the aqueous composition can comprise at least one diamine compound. Preferred diamide compounds are according to the general structure

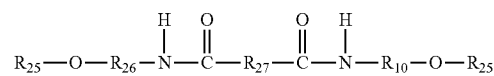

wherein $R_{25}$ is a linear or branched, saturated or unsaturated alkyl chain with 1 to 12 C atoms which may be substituted with hydroxy and/or alkoxy groups, preferably $R_{25}$ is linear or branched, saturated or unsaturated alkyl chain with 1 to 12 C atoms which may be substituted by 1 to 3 substituents selected from a hydroxy group and C1 to C6 alkoxy group, more preferably $R_{25}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{26}$ is linear or branched alkyl chain with 1 to 5 C atoms, preferably linear or branched alkyl chain with 1 to 5 C atoms and more preferably an alkyl chain with 2 to 3 C atoms, and $R_{27}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

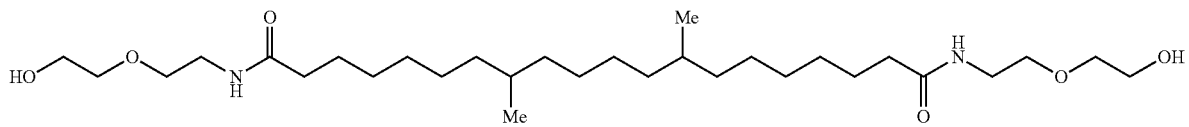

(A)

-continued

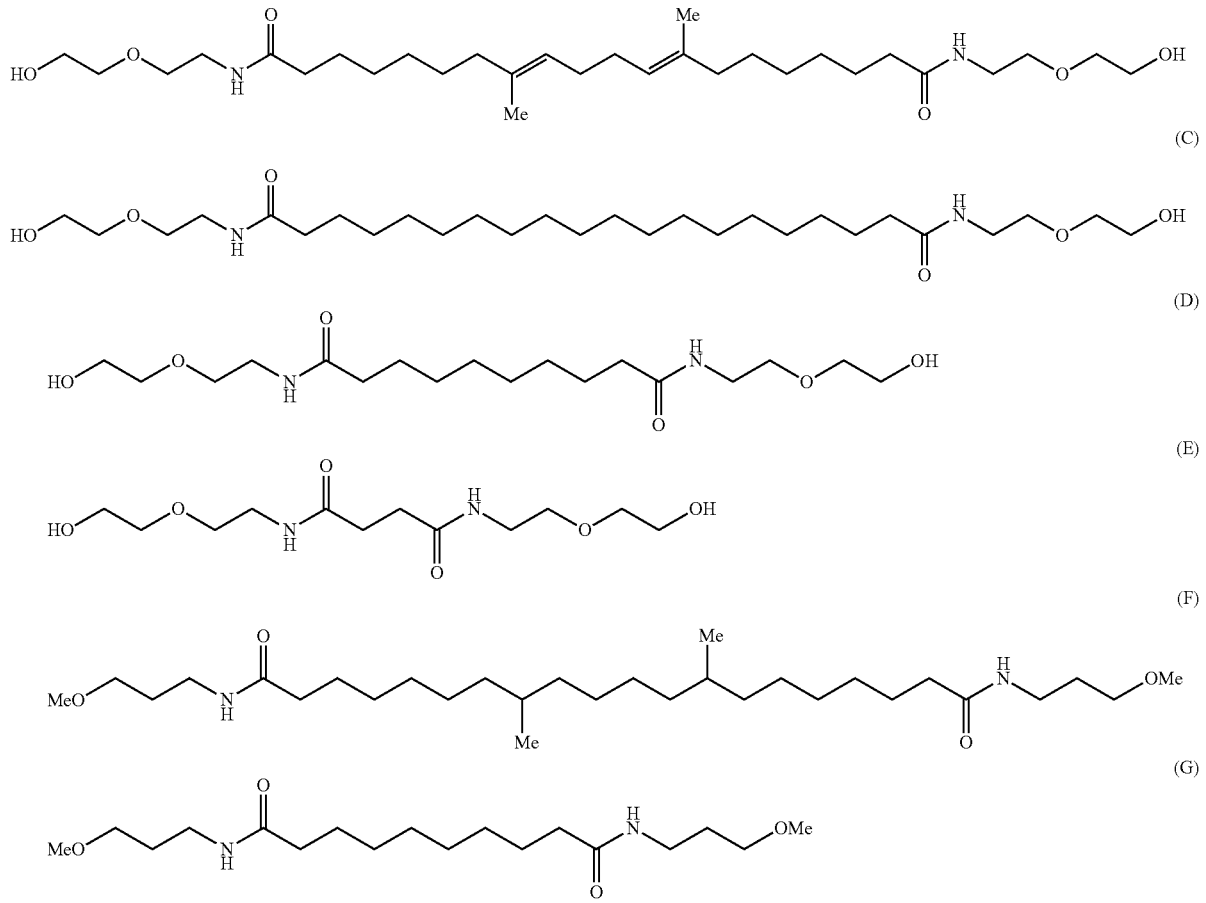

Particularly preferred diamide compound is the compound F which is bis (methoxypropylamido) isodocosane and commercially available from Kao Corporation-Japan.

Concentration of diamide compounds in the intermediate treatment compositions of the present invention is in the range of 0.001 to 5%, preferably 0.002 to 3% more preferably 0.005 to 2% and most preferably 0.01 to 1% by weight calculated to total of each composition.

Another preferred compound, one or more of the aqueous compositions comprise silicone compounds and especially aminated silicones such as amodimethicone available from for example Dow Corning under the brand names Dow Corning 949 Emulsion and Dow Corning 2-8194 ME. Concentration of silicones, especially amodimethicone, is in the range of 0.05 to 2.5%, preferably 0.1 to 1% by weight calculated to total or each composition.

Additionally, one or more natural oil may be incorporated into the one or more of the aqueous compositions of the present invention. Suitable are such as olive oil, almond oil, avocado oil, wheatgerm oil, ricinus oil or their mixture. Concentration of these natural oil ingredients should be 0.01 to 2.5%, preferably 0.01 to 1%, more preferably 0.05 to 0.5% by weight, calculated to total each composition.

The compositions used in the inventive process of the present invention are preferably provided in a kit. Accordingly further objective of the present invention is a kit for oxidative dyeing keratin fibers preferably hair comprising a—optionally an aqueous composition comprising at least one organic salt and/or dihydroxyacetone,
b—a composition comprising at least one hair dye wherein at least one hair dye is preferably selected from oxidative hair dye precursors and direct dyes which may be anionic, cationic and neutral dye,
c—an aqueous composition comprising at least one oxidizing agent, with the condition that at least one of the above compositions, preferably composition b, more preferably compositions b and c comprise a cross linked copolymer of vinylpyrrolidone, vinylimidazol, 3-methyl-1-vinylimidazolium and methacrylic acid, preferably Polyquaternium-86.

The following examples are to illustrate the invention, but not to limit it.

EXAMPLE 1

|  | % by weight |
|---|---|
| Stearyl alcohol | 8.0 |
| Coco fatty acid monoethanolamide | 4.5 |
| 1,2-Propanediol mono/distearate | 1.0 |
| Coco fatty alcohol polyglycol ether | 4.0 |
| Sodium lauryl sulphate | 1.0 |
| Oleic acid | 2.0 |

-continued

|  | % by weight |
|---|---|
| Propanediol | 2.0 |
| Sodium sulfite | 1.0 |
| Luvigel Advanced | 1.0 |
| Ascorbic acid | 0.5 |
| EDTA | 0.5 |
| Ammonia | 1.0 |
| p-toluenediamine sulhate | 0.74 |
| 4-chlorresorcinol | 0.24 |
| Resorcinol | 0.08 |
| m-aminophenol | 0.06 |
| 4-amino-2-hydroxytoluene | 0.02 |
| Water | to 100 |

The tests were carried out with swatches of bleached human hair. The coloring compositions were obtained after mixing the above given composition comprising dyestuff precursors with oxidizing agent comprising 4% by weight hydrogen peroxide at a mixing ratio of 1:1 by weight. The pH of the resulting mixture was 9.8.

Hair coloured with the above composition for 30 min at ambient temperature was homogeneously coloured. It was observed that hair was easily combable, soft, with natural bounce and elasticity and had less flyaways. Exclusion of Luvigel Advanced resulted in loss of effects.

EXAMPLE 2

The compositions of Example 1 were used wherein oxidizing composition comprising 4% by weight hydrogen peroxide comprised additionally 0.5% by weight Luvigel Advanced. Hair was coloured homogeneously and was combable, softer and had less flyaways. It was observed that shine was also significantly improved. Exclusion of Luvigel Advanced resulted in loss of effects.

EXAMPLE 3

The compositions of Example 1 were used
Additionally hair was treated first with a pretreatment composition of the following composition

|  | % by weight |
|---|---|
| Potassium iodide | 2.5 |
| Luvigel Advanced | 0.5 |
| Monoethanolamine | 4.8 |
| Hydrochloric acid | 4.0 |
| Water | q.s. to 100 | pH of the above composition was 8.0.

Hair was treated first with pretreatment composition of the above composition for 10 min and without rinsing off oxidative dyeing composition as in Example 1 was applied and after 30 min. rinsed off from hair and hair was dried. Hair was coloured homogeneously and was combable, soft and had less flyaways and had natural elasticity. It was observed that shine was also significantly improved. Exclusion of Luvigel Advanced resulted in loss of effects.

The invention claimed is:
1. A process for oxidative dyeing keratin fibers comprising:
mixing compositions A and B to form a mixture, wherein composition A comprises at least one oxidative dye precursor and, optionally, at least one coupling agent and, optionally, at least one direct dye in a cosmetically acceptable medium, and further wherein composition B comprises at least one oxidizing agent in a cosmetically acceptable medium; and
applying the mixture onto the keratin fibers and processing for 1 to 45 min at a temperature range of 20 to 45° C. and rinsing the mixture off from the keratin fibers,
wherein at least one of the two compositions A and B comprises a cross linked copolymer of vinylpyrrolidone, vinylimidazol, 3-methyl-1-vinylimidazolium and methacrylic acid.

2. The process according to claim 1, wherein both compositions A and B comprise a cross linked copolymer of vinylpyrrolidone, vinylimidazol, 3-methyl-1-vinylimidazolium and methacrylic acid.

3. The process according to claim 1, wherein the cross linked copolymer is Polyquaternium-86.

4. The process according to claim 1, wherein the cross linked copolymer is present at a concentration range of 0.01 to 10% by weight calculated to total of each composition.

5. The process according to claim 1, wherein composition A further comprises at least one alkalizing agent.

6. The process according to claim 1, wherein the mixture obtained after mixing of compositions A and B has a pH between 2 to 11.

7. The process according to claim 1, wherein composition B further comprises hydrogen peroxide as an oxidizing agent.

8. The process according to claim 1, wherein the mixture obtained after mixing of compositions A and B has a viscosity in the range of 1000 to 25000 mPa·s measured at 20° C. with Brookfield viscosi.

9. A process according to claim 1 further comprising:
applying onto the kerating fibres pretreatment composition comprising at least one compound, catalyzing or effecting the oxidative colour development reaction from oxidative dye precursors,
processing up to 20 min, and
optionally, rinsing off the pretreatment composition from keratin fibres prior to application of the mixture of compositions A and B.

10. The process according to claim 9, wherein the pretreatment composition comprises at least one inorganic salt and/or dihydroxyacetone as compound catalyzing and/or effecting the oxidative colour development reaction from oxidative dye precursors.

11. The process according to claim 9, wherein the pretreatment composition comprises a cross linked copolymer of vinylpyrrolidone, vinylimidazol, 3-methyl-1-vinylimidazolium and methacrylic acid.

12. The process according to claim 1, wherein one or more of the compositions A and B comprise one or more of the compounds selected from
surfactants,
conditioning agents,
ubiqinones of the formula

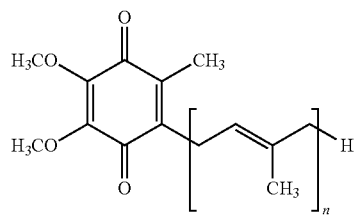

where n is a number between 1 and 10,
amino acid,
ceramide type of compound according to general formula

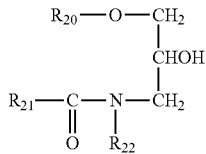

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6,
sterol, especially phytosterol,
diamide compounds according to general structure

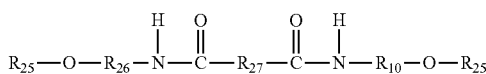

wherein $R_{25}$ is a linear or branched, saturated or unsaturated alkyl chain with 1 to 12 C atoms which may be substituted with hydroxy and/or alkoxy groups, preferably $R_{25}$ is linear or branched, saturated or unsaturated alkyl chain with 1 to 12 C atoms which may be substituted by 1 to 3 substituents selected from a hydroxy group and C1 to C6 alkoxy group, more preferably $R_{25}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{26}$ is linear or branched alkyl chain with 1 to 5 C atoms, and $R_{27}$ linear or branched, saturated or unsaturated alkyl chain with 1 to 22 C atoms,
silicone compound, and
natural oil.

13. A composition for dyeing keratin fibers comprising at least one hair dye and a cross linked copolymer of vinylpyrrolidone, vinylimidazol, 3-methyl-1-vinylimidazolium and methacrylic acid, wherein the at least one hair dye is selected from oxidative hair dye precursors and direct dyes selected from anionic, cationic and neutral dyes.

14. The composition according to claim 13, further comprising at least one oxidizing agent.

15. A kit for oxidative colouring keratin fibers comprising
a—optionally, an aqueous composition comprising at least one organic salt or dihydroxyacetone,
b—a composition comprising at least one hair dye wherein at least one hair dye is selected from oxidative hair dye precursors and direct dyes selected from anionic, cationic and neutral dyes, and
c—an aqueous composition comprising at least one oxidizing agent,
with the condition that at least one of the compositions a, b and c comprise a cross linked copolymer of vinylpyrrolidone, vinylimidazol, 3-methyl-1-vinylimidazolium and methacrylic acid.

* * * * *